(12) United States Patent
Otaka et al.

(10) Patent No.: US 6,423,745 B1
(45) Date of Patent: Jul. 23, 2002

(54) PYRETHROID COMPOUND AND COMPOSITION FOR CONTROLLING PEST CONTAINING THE SAME AS AN ACTIVE INGREDIENT

(75) Inventors: Ken Otaka; Takao Ishiwatari, both of Toyonaka (JP)

(73) Assignee: Sumitomo Chemical Co., Ltd., Osaka (JP)

( * ) Notice: Subject to any disclaimer, the term of this patent is extended or adjusted under 35 U.S.C. 154(b) by 0 days.

(21) Appl. No.: 09/306,785

(22) Filed: May 7, 1999

(30) Foreign Application Priority Data

May 26, 1998 (JP) ............................. 10-144080

(51) Int. Cl.[7] ................................ A01N 53/02
(52) U.S. Cl. ....................... 514/531; 424/405
(58) Field of Search ....................... 514/531; 424/405

(56) References Cited

U.S. PATENT DOCUMENTS 4,889,872 A 12/1989 Naumann et al.

FOREIGN PATENT DOCUMENTS

| GB | A2055822 | 3/1981 |
| HU | 203271 B | 7/1991 |

*Primary Examiner*—Neil S. Levy
(74) *Attorney, Agent, or Firm*—Stevens, Davis, Miller & Mosher, L.L.P.

(57) ABSTRACT

(S)-2-methyl-4-oxo-3-(2-propynyl)-cyclopent-2-enyl (1R)-trans-3-(2,2-dichlorovinyl)-2,2-dimethylcyclopropanecarboxylate represented by the formula:

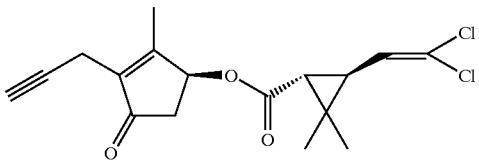

is a compound excellent in controlling effect on insect pests and harmlessness to mammals.

2 Claims, No Drawings

PYRETHROID COMPOUND AND COMPOSITION FOR CONTROLLING PEST CONTAINING THE SAME AS AN ACTIVE INGREDIENT

BACKGROUND OF THE INVENTION

It has been known that, for example, esters of haloalkenylcyclopropanecarboxylic acids and 2-methyl-4-oxo-3-(2-propynyl)-cyclopent-2-enyl alcohol have an insecticidal activity, see GB-2055822-A.

Application of such compositions containing the above esters, however, is often unavoidably limited not only by their controlling effect but also by their safety, depending on the application conditions. In particular, usually, compositions for controlling pest for preventing epidemics are used mainly in a limited space in a living environment and hence are required to have a desirable insecticidal or repellent activity as well as a marked harmlessness to mammals such as human beings, livestock and pets.

BRIEF SUMMARY OF THE INVENTION

In recognition of the situation, the present inventors have earnestly investigated and consequently found that a specific optically active trans-form of 2-methyl-4-oxo-3-(2-propynyl)-cyclopent-2-enyl 3-(2,2-dichlorovinyl)-2,2-dimethylcyclopropanecarboxylate is a compound excellent in controlling effect on pest and harmlessness to mammals, to accomplish the present invention.

Thus, the present invention relates to (S)-2-methyl-4-oxo-3-(2-propynyl)-cyclopent-2-enyl (1R)-trans-3-(2,2-dichlorovinyl)-2,2-dimethylcyclopropanecarboxylate (hereinafter referred to as the present compound) represented by the formula:

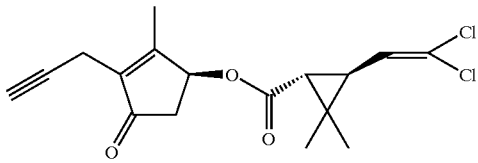

and a composition for controlling pest containing the present compound as an active ingredient.

The present compound can be produced, for example, by reacting (S)-2-methyl-4-oxo-3-(2-propynyl)-cyclopent-2-enyl alcohol (hereinafter referred to as the alcohol compound) represented by the formula:

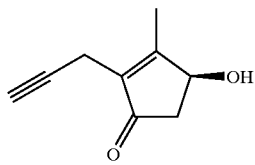

with (1R)-trans-3-(2,2-dichlorovinyl)-2,2-dimethylcyclopropanecarboxylic acid (hereinafter referred to as the carboxylic acid compound) represented by the formula:

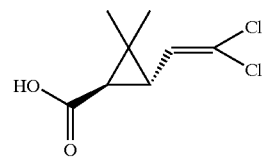

or a reactive derivative (e.g. acid halide or acid anhydride) of said carboxylic acid compound.

The reaction is usually carried out in a solvent in the presence of a condensing agent or a base.

The condensing agent includes, for example, dicyclohexylcarbodiimide (DCC) and 1-ethyl-3-(3-dimethylaminopropyl) carbodiimide hydrochloride (WSC).

The base includes, for example, organic bases such as triethylamine, pyridine, N,N-diethylaniline, 4-dimethylaminopyridine and diisopropylethylamine.

The solvent includes, for example, hydrocarbons such as benzene, toluene and hexane; ethers such as diethyl ether, and tetrahydrofuran; and halogenated hydrocarbons such as dichloromethane and 1,2-dichloroethane.

The reaction time ranges usually from 5 minutes to 72 hours.

The reaction temperature ranges usually from −20° C. to +100° C. (or from −20° C. to the boiling point of the solvent in the case where the boiling point of the solvent is lower than +100° C.), preferably from −5° C. to +100° C. (or from −5° C. to the boiling point of the solvent in the case where the boiling point of the solvent is lower than +100° C.).

Although the molar ratio of the carboxylic acid compound or its reactive derivative to the alcohol compound can be selected without any limitation, it is preferable to carry out the reaction by using them in an approximate molar ratio of 1:1.

The condensing agent or the base can be used in an arbitrary ratio to the alcohol compound, and is preferably used in an amount of 1 mole to 5 moles per mole of the alcohol compound.

The present compound can be obtained by subjecting the reaction solution after completion of the reaction to conventional after-treatments such as extraction with an organic solvent and concentration. If necessary, it can be further purified by conventional operations such as chromatography, distillation and recrystallization.

The alcohol compound can be produced according to, for example, the process disclosed in U.S. Patent No. 4,571,436, etc. The carboxylic acid compound can be produced according to, for example, the process disclosed in JP-A-4-234991, etc.

Examples of pests on which the present compound has controlling effect are the arthropods given below. Because the present compound can be used as an active ingredient of a composition for controlling the following arthropods and in particular is superior in safety factor, it is especially effective as the active ingredient of a composition for controlling pest for preventing epidemics, which is required to have a high safety to mammals.

Lepidoptera

Pyralidae (pyralid moths) such as *Chilo suppressalis* (rice stem borer), *CnaDhalocrocis medinalis* (rice leafroller) and *Plodia interpunctella* (Indian meal moth); Noctuidae such as *Spodoptera litura* (tobacco cutworm), *Pseudaletia separata* (rice armyworm) and *Mamestra brassicae* (cabbage armyworm); Pieridae such as *Pieris rapae crucivora* (common cabbageworm); Tortricidae (tortricid moths) such as Adoxophyes spp.; Carposinidae; Lyonetiidae (lyonetiid moths); Lymantriidae (tussock moths); Antographa spp.; Acrotis spp. such as *Agrothis segetum* (turnip cutworm) and *Agrothis ipsilon* (black cutworm); Helicoverpa spp.; Heliothis spp.; *Plutella xylostella* (diamondback moth); *Parnara guttata* (rice skipper); *Tinea translucens* (casemaking clothes moth); *Tineola bisselliella* (webbing clothes moth); *Plodia interpunctella* (Indian meal moth); etc.

Diptera

Culex spp. such as *Culex pipiens pallens* (common mosquito) and *Culex tritaeniorhvnchus*; Aedes spp. such as *Aedes aegypti* and *Aedes albopictus*; Anopheles spp. such as *Anopheles sinensis*; Chironomidae (midges); Muscidae such as *Musca domestica* (housefly), *Muscina stabulans* (false stablefly) and *Fannia canicularis* (little housefly); Calliphoridae; Sarcophagidae; Anthomyiidae (anthomylid flies) such as *Delia platura* (seedcorn maggot) and *Delia antigua* (onion maggot); Tephritidae (fruit flies); Drosophilidae (small fruit flies, vinegar flies); Psychodidae (moth flies, sand flies); Simuliidae (black flies); Tabanidae; Stomoxyidae (stable flies); biting midges; etc.

Dictyoptera

*Blattella germanica* (German cockroach), *Periplaneta fuliginosa* (smokybrown cockroach), *Periplaneta americana* (American cockroach), *Periplaneta brunnea* (brown cockroach), Blatta orientalis (oriental cockroach), etc.

Hymenoptera

Formicidae (ants); Vespidae (hornets); Bethylidae (bethylid wasps); Tenthredinidae (sawflies) such as *Athalia rosae ruficornis* (cabbage sawfly); etc.

Siphonaptera

*Ctenocephalides canis, Ctenocephalides felis, Pulex irritans,* etc.

Anoplura

*Pediculus humanus, Phthirus pubis,* etc.

Isoptera Termites

*Reticulitermes spereratus, Coptotermes formosanus* (Formosan subterranean termite), etc.

Acarina (Mites and Ticks)

Pyroglyphidae such as *Dermatophagoides farinae* and *Dermatophagoides pteronyssinus*; Acaridae such as *Tyrophagus putrescentiae* Schrank (mold mite, copra mite, forage mite) and *Aleurogalyphus ovatus* Troupeau (brown legged grain mite); Glycyphagidae such as *Glycyphagus privatus, Glycyphagus domesticus* and *Glycyphagus destructor* Schrank (groceries mite); Cheyletidae such as *Cheyletus malaccensis* and *Cheyletus moorei*; Tarsonemidae; Chrtoglyphus; Oribatei; Tetranychidae (spider mites) such as *Tetranychus urticae* (two-spotted spider mite), *Tetranvchus kanzawai* (Kanzawa spider mite), *Panonychus citri* (citrus red mite) and *Panonychus ulmi* (European red mite); Ixodidae such as *Haemaphysalis longicornis*; etc.

Hemiptera

Delphacidae (planthoppers) such as *Laodelphax striatellus* (small brown planthopper), *Nilaparvata lugens* (brown planthopper) and *Sogatella furcifera* (white-backed rice planthopper); Deltocephalidae (leaf-hoppers) such as *Nephotettix cincticeps* (green rice leafhopper) and *Nephotettix virescens* (green rice leafhopper); Aphididae (aphids); Pentatomidae (bugs); Aleyrodidae (whiteflies); Coccidae (scales); Tingidae (lace bugs); Psyllidae (psyllids); etc.

Coleoptera

*Attagenus unicolor; Anthrenus verbasci* (varied carpet beetle); corn rootworms such as *Diabrotica virgifera* (western corn rootworm) and *Diabrotica undecimpunctaca howardi* (southern corn rootworm); Scarabaeidae (scarabs) such as *Anomala cuprea* (cupreous chafer) and *Anomala rufocuprea* (soybean beatle); Curculionidae (weevils) such as *Sitophilus zeamais* (maize weevil), *Lissorhoptrus oryzophilus* (ricewater weevil), *Anthonomus grandis grandis* (boll weevil) and *Callosobruchus chinensis* (adzuki bean weevil); Tenebrionidae (darkling beetles) such as *Tenebrio molitor* (yellow mealworm) and *Tribolium castaneum* (red fluor beetle); Chrysomelidae (corn rootworms) such as *Oulema oryzae* (rice leaf beetle), *Phyllotreta striolata* (striped flea beetles) and *Aulacophora femoralis* (cucurbit leaf beetle); Anobiidae; Epilachna spp. such as *Henosepilachna vigintioctopunctata* (twenty-eight-spotted ladybirds); Lyctidae (powder post beetles); Bostrychidae (false powder post beetles); Cerambycidae; Paederus fuscipes (robe beetle); etc.

Thysanoptera (Thrips)

*Thrips palmi, Thrips hawaiiensis* (flower thrips), etc.

Orthoptera

Gryllotalpidae (mole crickets), Acrididae (grasshoppers), etc.

In the present invention, the composition for controlling pest is for controlling arthropods such as insects and/or acarines.

When the present compound is used as an active ingredient of the composition for controlling pest, it is applied usually after having been formulated into various formulations, for example, oil formulations; emulsifiable concentrates; wettable powders; flowable concentrates such as aqueous suspension concentrates and aqueous emulsion concentrates; granules; dusts; aerosols; heating fumigants such as mosquito coils, electric mosquito mats and solutions for heating fumigation using an absorbent wick; heating smoking formulations such as self-burning-type smoking formulations, chemical-reaction-type smoking formulations and electrically heating-type smoking formulations using a porous ceramic plate; non-heating volatile formulations such as resin volatile formulations and impregnated paper volatile formulations; foggings; ULV formulations; poisonous baits; or the like, usually by mixing the present compound or a solution thereof with a solid carrier, liquid carrier, gaseous carrier, base material for poisonous bait or base material for mosquito coil, and optionally adding auxiliaries for formulation such as surfactants, or alternatively by impregnating a base material such as a mosquito coil or mat with the present compound or a solution thereof.

These formulations usually contain the present compound as an active ingredient in an amount of 0.001 to 95% by weight.

The solid carrier used for formulation includes, for example, fine powders and granules of inorganic carriers such as clays (e.g. kaolin clay, diatomaceous earth, synthetic hydrated silicon dioxide, bentonite, fubasami clay and acid clay), talcs, ceramics, sericite, quartz and calcium carbonate; synthetic resins such as polyethylenes and polypropylenes; and carriers obtained from plants such as wood powder and activated carbon. The liquid carrier includes, for example, water, alcohols (e.g. methanol, ethanol and higher alcohols), ketones (e.g. acetone and methyl ethyl ketone), aromatic hydrocarbons (e.g. benzene, toluene, xylene, ethylbenzene and methylnaphthalene), aliphatic hydrocarbons (e.g. hexane, cyclohexane, kerosene and light oil), esters (e.g. ethyl acetate and butyl acetate), nitriles (e.g. acetonitrile and isobutyronitrile), ethers (e.g. diisopropyl ether and dioxane), acid amides (e.g. N,N-dimethylformamide and N,N-dimethylacetamide), halogenated hydrocarbons (e.g. dichloromethane, trichloroethane and carbon tetrachloride), dimethyl sulfoxide and vegetable oils (e.g. soybean oil and cotton seed oil). The liquefied gas carrier includes, for example, fluorocarbon, fluorohydrocarbon, LPG (liquefied petroleum gas), dimethyl ether and carbon dioxide.

The surfactant includes, for example, alkyl sulfates, alkylsulfonates, alkylarylsulfonates, alkyl aryl ethers and their polyoxyethylenated products, polyethylene glycol ethers, polyhydric alcohol esters and sugar alcohol derivatives.

The auxiliaries for formulation such as adhesive agents and dispersants include, for example, casein, gelatin, polysaccharides (e.g. starch powder, gum arabic, cellulose derivatives and alginic acid), lignin derivatives, bentonite, saccharides and synthetic water-soluble polymers [e.g. poly (vinyl alcohol)s, poly(vinylpyrrolidone)s and poly(acrylic acid)s]. Examples of stabilizer are PAP (acidic isopropyl phosphate), BHT (2,6-di-tert-butyl-4-methylphenol), BHA (a mixture of 2-tert-butyl-4-methoxyphenol and 3-tert-butyl-4-methoxyphenol), vegetable oils, mineral oils, surfactants and fatty acids or their esters.

Base materials for the mosquito coils include, for example, mixtures of vegetable powders (e.g. wood powder and Pyrethrum marc) and binders (e.g. Tabu powder, starch and gluten).

Base materials for electric mosquito mats include, for example, plates obtained by coagulating fibrils of cotton linter or a mixture of cotton linter and pulp.

Base materials for self-burning-type smoking formulations include, for example, combustible and heat-generating agents (e.g. nitrates, nitrites, guanidine salts, potassium chlorate, nitrocellulose, ethylcellulose and wood powder), pyrolysis-promoting agents (e.g. alkali metal salts, alkaline earth metal salts, dichromates and chromates), oxygen-supplying agents (e.g. potassium nitrate), combustion-supporting agents (melamine and wheat starch), extending agents (e.g. diatomaceous earth) and binders (e.g. synthetic pastes).

Base materials for the chemical-reaction-type smoking formulations include, for example, heat-generating agents (e.g. sulfides, polysulfides, hydrosulfides and hydrate salts of alkali metals, and calcium oxide), catalysts (e.g. carbonaceous substances, iron carbide and activated clay), organic foaming agents (e.g. azodicarbonamide, benzenesulfonylhydrazide, dinitrosopentamethylenetetramine, polystyrenes and polyurethanes) and fillers (e.g. natural fiber pieces and synthetic fiber pieces).

Base materials for the non-heating volatile formulations include, for example, thermoplastic resins, filter papers and Japanese papers.

The base material for poisonous baits includes, for example, bait components (e.g. cereal flour, vegetable oils, saccharides and crystalline cellulose), antioxidants (e.g. dibutylhydroxytoluene and nordihydroguaiaretic acid), preservatives (e.g. dehydroacetic acid), agents for preventing consumption by children or pets (e.g. red pepper powder), and attractants (e.g. cheese perfume, onion perfume and peanut oil).

The flowable concentrates (aqueous suspension concentrates or aqueous emulsion concentrates) usually comprise the present compound, a dispersant, a suspension assistant (e.g. a protective colloid or a compound capable of imparting thixotropic properties), suitable auxiliaries (e.g. defoaming agents, rust preventives, stabilizers, spreaders, penetration assistants, anti-freezing agents, bactericides and fungicides) and water. The protective colloid includes, for example, gelatin, casein, gums, cellulose ether and poly (vinyl alcohol)s. The compound capable of imparting thixotropic properties includes, for example, bentonite, aluminum magnesium silicate, xanthan gum and poly(acrylic acid)s. It is also possible to prepare an oil-based suspension concentrate by using an oil substantially incapable of dissolving the present compound, in place of water.

The formulations thus obtained are applied as they are or after diluted with water or the like, depending on the purposes.

It is also possible to apply the formulations in admixture or combination with other insecticides, acaricides, repellents, synergists or the like.

The insecticides and acaricides include, for example, organophosphorus compounds such as Fenitrothion [O,O-dimethyl O-(3-methyl-4-nitrophenyl)phosphorothioate], Fenthion[O,O-dimethyl O-(3-methyl-4-(methylthio) phenyl)-phosphorothioate], Diazinon [O,O-diethyl O-2-isopropyl-6-methylpyrimidin-4-ylphosphorothioate], Chlorpyrifos[O,O-diethyl O-3,5,6-trichloro-2-pyridylphosphorothioate], Acephate[O,S-dimethylacetylphosphoramidothioate], methidathion[S-2,3-dihydro-5-methoxy-2-oxo-1,3,4-thiadiazol-3-ylmethyl O,O-dimethylphosphorodithioate], Disulfoton[O,O-diethyl S-2-ethylthioethyl-phosphorodithioate], DDVP [2,2-dichlorovinyldimethyl phosphate], Sulprofos [O-ethyl O-4-(methylthio)phenyl S-propylphosphorodithioate], Cyanophos [O-4-cyanophenyl O,O-dimethylphosphorothioate], Dioxabenzophos [2-methoxy-4H-1,3,2-benzodioxaphosphorine-2-sulfide], Dimethoate [O,O-dimethyl S-(N-methylcarbamoylmethyl) dithiophosphate], Phenthoate [ethyl 2-dimethoxyphosphinothioylthio-(phenyl)acetate], Malathion [diethyl (dimethoxy-phosphinothioylthio) succinate], Trichlorfon [dimethyl 2,2,2,-trichloro-1-hydroxyethylphosphonate], Azinphosmethyl [S-3,4-dihydro-4-oxo-1,2,3-benzotriazin-3-ylmethyl O,O-dimethylphosphorodithioate], Monocrotophos [dimethyl (E)-1-methyl-2-(methylcarbamoyl)vinylphosphate] and Ethion [O,O,O',O'-tetraethyl S,S'-methylenebis(phosphorodithioate)]; carbamate type compounds such as BPMC [2-sec-butylphenylmethylcarbamate], Benfuracarb [ethyl N-[2,3-dihydro-2,2-dimethylbenzofuran-7-yloxycarbonyl (methyl)-aminothio]-N-isopropyl-β-alaninate], Propoxur [2-isopropoxyphenyl N-methylcarbamate], Carbosulfan [2,3-dihydro-2,2-dimethyl-7-benzo[b]furanyl N-dibutylaminothio-N-methylcarbamate], Carbaryl [1-naphthyl-N-methyl-carbamate], Methomyl [S-methyl-N-[(methylcarbamoyl)oxy] thioacetimidate], Ethiofencarb [2-(ethylthiomethyl)-phenylmethylcarbamate], Aldicarb [2-methyl-2-(methylthio)propionaldehyde O-methycarbamoyloxime], Oxamyl [N,N-dimethyl-2-methylcarbamoyloxyimino-2-(methylthio)acetamide] and Phenothiocarb [(S-4-phenoxybutyl)-N,N-dimethylthiocarbamate]; pyrethroid compounds such as Etofenprox [2-(4-ethoxyphenyl)-2-methylpropyl-3-phenoxybenzyl ether), Fenvalerate [(RS)-α-cyano-3-phenoxybenzyl (RS)-2-(4-chlorophenyl)-3-5 methylbutyrate], Esfenvalerate [(S) -α-cyano-3-phenoxybenzyl (S)-2-(4-chlorophenyl)-3-methylbutyrate], Fenpropathrin [(RS)-α-cyano-3-phenoxybenzyl 2,2,3,3-tetramethylcyclo-propanecarboxylate], Cypermethrin [(RS)-α-cyano-3-phenoxybenzyl (1RS)-cis,trans-3-(2,2-dichlorovinyl)-2,2-dimethylcyclopropanecarboxylate], Permethrin [3-phenoxybenzyl (1RS)-cis,trans-3-(2,2-dichlorovinyl)-2,2-dimethylcyclopropanecarboxylate], Cyhalothrin [(RS)-α-cyano-3-phenoxybenzyl (Z)-(1RS)-cis-3-(2-chloro-3,3,3-trifluoroprop-1-enyl)-2,2-dimethylcyclopropanecarboxylate], Deltamethrin [(S)-α-cyano-3-phenoxybenzyl (1R)-cis-3-(2,2-dibromovinyl)-2,2-dimethylcyclopropanecarboxylate], Cycloprothrin [(RS)-α-cyano-3-phenoxybenzyl (RS)-2,2- dichloro-1-(4-ethoxyphenyl)cyclopropanecarboxylate], Fluvalinate [α-cyano-3-phenoxybenzyl N-(2-chloro-α, α, α-trifluoro-p-tolyl)-D-valinate], Bifenthrin [(2-methylbiphenyl-3-ylmethyl) (Z)-(1RS)-cis-3-(2-chloro-3,3,3-trifluoroprop-1-enyl)-2,2-dimethylcyclopropanecarboxylate], 2-methyl-2-(4-bromodifluoromethoxyphenyl)propyl (3-phenoxybenzyl) ether, Tralomethrin [(S)-α-cyano-3-phenoxybenzyl (1R-cis)3 {(1RS)-(1,2,2,2-tetrabromoethyl) }-2,2-dimethylcyclopropanecarboxylate], [4-ethoxyphenyl{3-(4-fluoro-3-phenoxyphenyl)propyl} dimethylsilane], d-Phenothrin [3-phenoxybenzyl (1R-cis,trans)-chrysanthemate], [(RS)-α-cyano-3-phenoxybenzyl (1R-cis,trans)-chrysanthemate], d-Resmethrin [5-benzyl-3-furylmethyl (1R-cis,trans)-chrysanthemate], [(S) -α-cyano-3-phenoxybenzyl (1R-cis(Z))-(2,2-dimethyl-3- {3-oxo-3-(1,1,1,3,3, 3-hexafluoropropyloxy)propenyl} cyclopropanecarboxylate], Cyfluthrin [(RS)-α-cyano-4-fluoro-3-phenoxybenzyl 3-(2,2-dichlorovinyl)-2,2-dimethylcyclopropanecarboxylate], Tefluthrin [2,3,5,6-tetrafluoro-4-methylbenzyl (1RS-cis(Z))-3-(2-chloro-3,3,3-trifluoroprop-1-enyl)-2, 2-dimethylcyclopropanecarboxylate], Transfluthrin [2,3,5,6-tetrafluorobenzyl (1R-trans)-3-(2,2-dichlorovinyl)-2,2-dimethylcyclopropanecarboxylate], Tetramethrin [3,4,5,6-tetrahydrophthalimidomethyl (1RS)-cis,trans-chrysanthemate], Allethrin [(RS)-3-allyl-2-methyl-4-oxocyclopent-2-enyl (1RS)-cis,trans-chrysanthemate], Prallethrin [(S)-2-methyl-4-oxo-3-(2-propynyl)cyclopent-2-enyl (1R)-cis,trans-chrysanthemate], Empenthrin [(RS)-1-ethynyl-2-methyl-2-pentenyl (1R)-cis,trans-chrysanthemate], Imiprothrin [2,5-dioxo-3-(prop-2-ynyl) imidazolidin-1-ylmethyl (1R)-cis,trans-2,2-dimethyl-3-(2-methylprop-1-enyl)cyclopropanecarboxylate], d-Flamethrin [5-(2-propynyl)furfuryl (1R)-cis,trans-chrysanthemate], and 5-(2-propynyl)furfuryl 2,2,3,3-tetramethylcyclopropane-carboxylate]; N-cyanoamidine derivatives such as N-cyano-N'-methyl-N'-(6-chloro-3-pyridylmethyl)acetoamidine; chlorinated hydrocarbon compounds such as Endosulfan [6,7,8,9,10,10-hexachloro-1,5,5a, 6,9,9a-hexahydro-6,9-methano-2,4,3-benzodioxathiepin oxide], γ-BHC [1,2,3,4,5,6-hexachlorocyclohexane], 1,1-bis(chlorophenyl)-2,2,2-trichloroethanol; benzoylphenylurea type compounds such as Chlorfluazuron [1-(3,5-dichloro-4-(3-chloro-5-trifluoromethylpyridin-2-yloxy)phenyl)-3-(2,6-difluorobenzoyl)urea], Teflubenzron [1-(3,5-dichloro-2,4-difluorophenyl)-3-(2, 6-difluorobenzoyl)urea], [1-(4-(2-chloro-4-trifluoromethylphenoxy)-2-fluorophenyl)-3-(2,6-difluorobenzoyl)urea]; thiourea derivatives such as [N-(2,6-diisopropyl-4-phenoxyphenyl)-N'-tert-butylcarbodi-imide]; phenylpyrazole type compounds; Metoxadiazon [5-methoxy-3-(2-methoxyphenyl)-1, 3,4-oxadiazol-2-(3H)-one], Bromopropylate [isopropyl 4,4'-dibromobenzilate]; Tetradifon [4-chlorophenyl 2,4,5-trichlorophenylsulfone]; Quinomethionate [S,S-6-methylquinoxaline-2,3-diyldithiocarbonate]; Pyridaben [2-tert-butyl-5-(4-tert-butylbenzylthio)-4-chloropyridazin-3(2H)-one]; Fenpyroximate [tert-butyl(E)-4-[(1,3-dimethyl-5-phenoxypyrazol-4-yl)methyleneaminoxymethyl] benzoate]; [N-4-tert-butylbenzyl)-4-chloro-3-ethyl-1-methyl-5-pyrazolecarboxamide]; Polynactin complexes [tetranactin, dinactin and trinactin]; Pyrimidifen [5-chloro-N-[2-{4-(2-ethoxyethyl)-2,3-dimethylphenoxyl} ethyl]-6-ethylpyrimidine-4-amine]; Milbemectin; Abamectin; ivermectin; azadirachtin [AZAD]; etc.

The repellents include, for example, 3,4-caranediol, N,N-diethyl-m-toluamide, 1-methylpropyl 2-(2-hydroxyethyl)-l-piperidinecarboxylate, p-menthane-3,8-diol, and plant essential oils such as hyssop oil.

The synergists include, for example, bis-(2,3,3,3-tetrachloropropyl) ether (S-421), N-(2-ethylhexyl)bicyclo-[2.2.1]hept-5-ene-2,3-dicarboximide (MGK-264), and α-[2-(2-butoxyethoxy)ethoxy]-4,5-methylenedioxy-2-propyltoluene (piperonyl butoxide).

When the present compound is used as an active ingredient of a composition for controlling pest for preventing domestic epidemics or for controlling pest for animals, formulations in the form of emulsifiable concentrates, wettable powders or flowable concentrates are applied usually after having been diluted with water so that the formulations have a concentration of the present compound falling within the range of from 0.1 to 10,000 ppm. Formulations in the form of oil formulations, aerosols, fumigants, smoking formulations, volatile formulations, foggings, ULV formulations, poisonous baits or resin formulations are applied as they are.

Both the applying dosage and the applying concentration of the above formulations can be properly determined depending on conditions such as the type of formulation, when, where and how these formulations are applied, kind of pests, degree of damage, etc.

EXAMPLES

The present invention is illustrated with reference to the following production example, formulation examples and test examples, which should not be construed as limiting the scope of the invention.

Firstly, an example of production of the present compound is described.

Production Example 3.4 Grams of pyridine was added to a mixture of 5.0 g of (S)-2-methyl-4-oxo-3-(2-propynyl)-cyclopent-2-enyl alcohol, 8.0 g of (1R)-trans-3-(2, 2-dichlorovinyl)-2,2-dimethylcyclopropanecarboxylic acid chloride and 50 ml of toluene under ice-cooling. The resulting mixture was allowed to react at room temperature for 12 hours. Thereafter, about 50 ml of a saturated aqueous ammonium chloride solution was added to the resultant reaction solution, which was then extracted with three 50-ml portions of diethyl ether. The combined diethyl ether layer was washed with a saturated aqueous sodium chloride solution, dried over anhydrous sodium sulfate and then concentrated under reduced pressure. The residue was subjected to a silica gel column chromatography followed by recrystallization from a mixed solvent of hexane and ethyl acetate to obtain 8.9 g (yield: 78%) of (S)-2-methyl-4-oxo-3-(2-propynyl)-cyclopent-2-enyl (1R)-trans-3-(2,2-dichlorovinyl)-2,2-dimethylcyclopropanecarboxylate (the present compound).

$^1$H-NMR (CDCl$_3$, TMS internal standard) δ values (ppm): 1.21(s, 3H), 1.29(s, 3H), 1.64(d, 1H), 2.00(t, 1H), 2.18(bs, 3H), 2.2–2.3(m, 2H), 2.92(dd, 1H), 3.16(d, 2H), 5.64(d, 1H), 5.71(bd, 1H).

The present compound obtained above is essentially free from (1R)-cis isomer and is utilized for Test Examples below.

Next, formulation examples are described below. In the formulation examples, parts are all by weight.

Formulation Example 1

A 20% emulsifiable concentrate is obtained by dissolving 20 parts of the present compound in 65 parts of xylene, and adding thereto 15 parts of an emulsifier Sorpol 3005X (a registered trade name, Toho Chemical Co., Ltd.), and thoroughly stirring and mixing the resultant mixture.

Formulation Example 2

A 40% wettable powder is obtained by thoroughly mixing 40 parts of the present compound with 5 parts of Sorpol 3005x (described above), and adding thereto 32 parts of Carplex #80 (a registered trade name, Shionogi & Co., Ltd.; fine powder of synthetic hydrated silicon dioxide) and 23 parts of 300-mesh diatomaceous earth, and stirring and mixing the resultant mixture in a juice mixer.

Formulation Example 3

1.5% Granules are obtained by thoroughly mixing 1.5 parts of the present compound with 98.5 parts of AGSORBLVM-MS 24/48 (a calcined product of montmorillonite, mfd. by OIL DRI Corp.; a granular carrier with a particle size of 24 to 48 mesh).

Formulation Example 4

A mixture of 10 parts of the present compound, 10 parts of phenylxylylethane and 0.5 part of Sumidur L-75 (tolylene diisocyanate, mfd. by Sumitomo Bayer Urethane Comp., Ltd.) is added to 20 parts of a 10% aqueous gum arabic solution. The resulting mixture is stirred in a homomixer to obtain an emulsion having an average particle size of 20 $\mu$m. Then, 2 parts of ethylene glycol is added to the emulsion. The resultant mixture is allowed to react on a hot bath at 60° C. for 24 hours to obtain a microcapsule slurry. On the other hand, 0.2 part of xanthan gum and 1.0 part of Veegum R (aluminum magnesium silicate, mfd. by Sanyo Chemical Industries Ltd.) are dispersed in 56.3 parts of ion-exchanged water to obtain a thickening agent solution.

42.5 Parts of the microcapsule slurry prepared above and 57.5 parts of the thickening agent solution prepared above are mixed to obtain 10% microcapsules.

Formulation Example 5

A mixture of 10 parts of the present compound and 10 parts of phenylxylylethane is added to 20 parts of a 10% poly(ethylene glycol) aqueous solution. The resulting mixture is stirred in a homomixer to obtain an emulsion having an average particle size of 3 $\mu$m. On the other hand, 0.2 part of xanthan gum and 1.0 part of Veegum R (aluminum magnesium silicate, mfd. by Sanyo Chemical Industries Ltd.) are dispersed in 58.8 parts of ion-exchanged water to obtain a thickening agent solution.

40 Parts of the emulsion prepared above and 60 parts of the thickening agent solution prepared above are mixed to obtain a 10% flowable concentrate.

Formulation Example 6

A 5% dust is obtained by stirring and mixing 5 parts of the present compound, 3 parts of Carplex #80 (a registered trade name, Shionogi & Co., Ltd.; fine powder of synthetic hydrated silicon dioxide), 0.3 part of PAP and 91.7 parts of 300-mesh talc in a juice mixer.

Formulation Example 7

A 0.1% oil formulation is obtained by dissolving 0.1 part of the present compound in 10 parts of dichloromethane and mixing the resulting solution in 89.9 parts of M (an isoparaffin, mfd. by Exxon Chemical Co.).

Formulation Example 8

An oil-based aerosol is obtained by mixing 1 part of the present compound, 5 parts of dichloromethane and 34 parts of deodorized kerosene to obtain a solution, charging the solution into an aerosol container, attaching a valve part to the container, and then compressing 60 parts of a propellant (liquefied petroleum gas) into the container under pressure through the valve part.

Formulation Example 9

A water-based aerosol is obtained by mixing 0.6 part of the present compound, 5 parts of xylene, 3.4 parts of deodorized kerosene and 1 part of an emulsifier {Atmos 300 (a registered trade name, Atlas Chemical Corp.)} to obtain a solution, charging the solution with 50 parts of pure water into an aerosol container, attaching a valve part to the container, and then compressing 40 parts of a propellant (liquefied petroleum gas) into the container under pressure through the valve part.

Formulation Example 10

A mosquito coil is obtained by dissolving 0.1 g of the present compound in 20 ml of acetone, stirring and mixing uniformly the resulting solution with 99.9 g of a carrier for mosquito coil (a mixture of Tabu powder, Pyrethrum marc and wood powder in the ratio of 4:3:3), adding thereto 120 ml of water, thoroughly kneading the resulting mixture, and molding and drying the kneaded mixture.

Formulation Example 11

0.2 Gram of the present compound and 0.4 g of piperonyl butoxide are dissolved in acetone to obtain a solution having a total volume of 10 ml. A base material for electric mat (a plate obtained by coagulating fibrils of a mixture of cotton linter and pulp) having an area of 2.5 cm×1.5 cm and a thickness of 0.3 cm is uniformly impregnated with 0.5 ml of the solution prepared above, to obtain an electric mosquito mat.

Formulation Example 12

A part used for an absorbent-wick type heating vaporization device is obtained by dissolving 3 parts of the present compound in 97 parts of deodorized kerosene to obtain a solution, placing the solution in a container made of vinyl chloride, and inserting one end of an absorbent wick (obtained by coagulating inorganic powder with a binder and baking the coagulated powder) into the container so that the other end of the wick can be heated with a heater.

Formulation Example 13

A heating smoking formulation is obtained by dissolving 100 mg of the present compound in an adequate amount of acetone to obtain a solution, and impregnating a porous ceramic plate having an area of 4.0 cm square and a thickness of 1.2 cm with the solution.

Formulation Example 14

An acarine-controlling sheet is obtained by impregnating a filter paper with a solution of the present compound in acetone so that the filter paper contains the present compound in a concentration of 1 gram per square meter, and air-drying the filter paper to remove the acetone.

Test Example 1

Effect of a mosquito coil on common mosquito
(*Culex pipiens pallens*)

A base material for mosquito coil (obtained by stirring a 4:3:3 mixture of Tabu powder, Pyrethrum marc and wood powder, adding water thereto, thoroughly kneading the resulting mixture, and molding and drying the kneaded mixture) was uniformly impregnated with a solution of the present compound in acetone so that the material contains a predetermined amount of the compound. The resultant base material was air-dried to obtain a mosquito coil.

Ten female adult common mosquitoes were released in a glass chamber (70 cm cube, capacity: 0.34 $m^3$). 0.3 Gram of a mosquito coil containing the present compound prepared according to the procedure described above was set on a holder in the center of bottom of the chamber, ignited at one end thereof, and taken out of the chamber after 30 seconds of combustion. The knocked-down common mosquitoes were counted in fifteen minutes after the setting of the coil.

The same test procedure was repeated for (S)-2-methyl-4-oxo-3-(2-propynyl)-cyclopent-2-enyl (1RS)-cis-3-(2,2-dichlorovinyl)-2,2-dimethylcyclopropanecarboxylate (hereinafter referred to as reference compound A).

Table 1 shows the results. In Table 1, the knocking-down activity is indicated according to the following criterion:

Excellent: All the insects were knocked down (the total in the two replications).

Good: 1 to 3 insects were not knocked down (ditto).

Mediocre: 4 to 6 insects were not knocked down (ditto).

Bad: 7 or more insects were not knocked down (ditto).

TABLE 1

| Test compound | Concentration (% W/W) | Knocking-down activity |
| --- | --- | --- |
| Present compound | 0.5 | Excellent |
| Reference compound A | 0.5 | Bad |
|  | 1.0 | Bad |

Test Example 2

Effect of spraying of an oil formulation on common mosquito (*Culex pipiens pallens*)

Ten female adult common mosquitoes were released in a glass chamber (70 cm cube, capacity: 0.34 m$^3$). 0.7 Milliliter of an oil formulation containing a predetermined concentration (shown in Table 2) of the present compound prepared according to Formulation Example 7 was sprayed into the chamber through a small side window of the chamber with a spray gun. The knocked-down common mosquitoes were counted in two minutes after the spraying.

The same test procedure was repeated for (S)-2-methyl-4-oxo-3-(2-propynyl)-cyclopent-2-enyl (1RS)-cis-3-(2,2-dichlorovinyl)-2,2-dimethylcyclopropanecarboxylate (hereinafter referred to as reference compound A).

Table 2 shows the results. In Table 2, the knocking-down activity is indicated according to the following criterion:

Good: 3 or less insects were not knocked down (the total in the two replications).

Mediocre: 4 to 6 insects were not knocked down (ditto).

Bad: 7 or more insects were not knocked down (ditto).

TABLE 2

| Test compound | Concentration (%W/W) | Knocking-down activity |
| --- | --- | --- |
| Present compound | 0.025 | Good |
| Reference compound A | 0.025 | Bad |
|  | 0.05 | Bad |

Test Example 3

Insecticidal Activity Against American Cockroach (*Periplaneta americana*) and Toxicity to Rat
Insecticidal Activity Against American Cockroach Each of the present compound and reference compound A were diluted with acetone to prepare dilutions of prescribed concentrations. Each dilution was applied on the sterna of female adult American cockroaches with a micro-applicator in a volume of 1.0 µl per insect. Then, the insects were given water and diet. After 72 hours, the dead and alive were counted. From the mortality, LD$_{50}$ (mg/kg) value was determined.

Toxicity to Rat

Each of the present compound and reference compound A was diluted with corn oil to predetermined concentrations. Each of the dilutions thus prepared was administered to male rats in an amount of 10 ml/kg. The rats were given water and diet. After 7 days, the dead and alive were counted for mortality. From the mortality, LD$_{50}$ (mg/kg) value was determined.

Calculation of Safety Factor

The safety factor was calculated from the insecticidal activity against American cockroach and the toxicity to rat according to the following equation. Table 3 shows the results.

Safety factor=[Toxicity to rat (LD$_{50}$ value)]/[Insecticidal activity against American cockroach (LD$_{50}$ value)]

TABLE 3

| Test compound | Insecticidal activity against American cockroach (LD$_{50}$) | Toxicity to rat (LD$_{50}$) | Safety factor |
| --- | --- | --- | --- |
| Present compound | 0.72 | >300 | >420 |
| Reference compound A | 4.4 | <100 | <23 |

The present compound is excellent in controlling effect on insect pests and safety to mammals and hence is very effective as the active ingredient of compositions for controlling insect pest, in particular, compositions for controlling insect pest for preventing epidemics.

What is claimed is:

1. A method for controlling arthropods, which comprises applying an artiropod-controiling effective amount of (S)-2-methyl-4oxo-3-(2-propynyl)-cyclopent-2-enyl (1R)-trans-3-(2,2-dichlorovinyl)-2,2-dimethylcyclopropanecarboxylate represented by the formula:

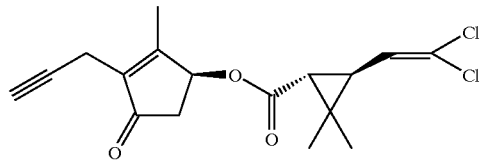

and essentially free from (1R)-cis isomer to the arthropods or a locus where the arthropods inhabit.

2. The method according to claim 1, wherein the arthropods are insects.

* * * * *